US012582212B2

(12) United States Patent
Cho et al.

(10) Patent No.: US 12,582,212 B2
(45) Date of Patent: Mar. 24, 2026

(54) MESH-TYPE MOISTURE-RELEASE CUSHION COSMETIC PRODUCT

(71) Applicant: INTERCOS KOREA INC.,
Gyeonggi-do (KR)

(72) Inventors: Ju Young Cho, Gyeonggi-do (KR); Yu Ji Hwang, Chungcheongnam-do (KR); Kwang Mo Yang, Gyeonggi-do (KR)

(73) Assignee: INTERCOS KOREA INC.,
Gyeonggi-do (KR)

( * ) Notice: Subject to any disclaimer, the term of this patent is extended or adjusted under 35 U.S.C. 154(b) by 757 days.

(21) Appl. No.: 17/283,440

(22) PCT Filed: Oct. 8, 2019

(86) PCT No.: PCT/KR2019/013211
§ 371 (c)(1),
(2) Date: Apr. 7, 2021

(87) PCT Pub. No.: WO2020/076059
PCT Pub. Date: Apr. 16, 2020

(65) Prior Publication Data
US 2021/0345755 A1     Nov. 11, 2021

(30) Foreign Application Priority Data

Oct. 10, 2018     (KR) ........................ 10-2018-0120175

(51) Int. Cl.
| | |
|---|---|
| A45D 34/04 | (2006.01) |
| A45D 33/00 | (2006.01) |
| A61K 8/02 | (2006.01) |
| A61K 8/06 | (2006.01) |
| A61K 8/60 | (2006.01) |
| A61K 8/894 | (2006.01) |

(52) U.S. Cl.
CPC ........... *A45D 34/04* (2013.01); *A45D 33/005* (2013.01); *A61K 8/0254* (2013.01); *A61K 8/064* (2013.01); *A61K 8/602* (2013.01); *A61K 8/894* (2013.01); *A45D 2200/1018* (2013.01); *A61K 2800/43* (2013.01); *A61K 2800/48* (2013.01); *A61K 2800/651* (2013.01)

(58) Field of Classification Search
None
See application file for complete search history.

(56) References Cited

U.S. PATENT DOCUMENTS

| | | | | |
|---|---|---|---|---|
| 2003/0213409 A1* | 11/2003 | DeLuca, Jr. | .......... | C09C 1/0018 |
| | | | | 106/439 |
| 2018/0250220 A1* | 9/2018 | Jeong | ................... | A61Q 19/007 |
| 2018/0271251 A1 | 9/2018 | Yeo | | |

FOREIGN PATENT DOCUMENTS

| | | | | | |
|---|---|---|---|---|---|
| EP | 3375825 | A1 | 9/2018 | | |
| EP | 3603615 | A1 | 2/2020 | | |
| JP | 2004-083500 | A | 3/2004 | | |
| JP | 2014-97936 | A | 5/2014 | | |
| JP | 2015-513987 | A | 5/2015 | | |
| JP | 2018-517747 | A | 7/2018 | | |
| KR | 10-1477583 | B1 | 12/2014 | | |
| KR | 10-1541396 | B1 | 8/2015 | | |
| KR | 101678559 | B1 | * 11/2016 | .............. | A61K 8/06 |
| KR | 10-2017-0027666 | A | 3/2017 | | |
| KR | 10-2017-0055580 | A | 5/2017 | | |
| KR | 10-1737880 | B1 | 7/2017 | | |
| KR | 10-2017-0125598 | A | 11/2017 | | |
| KR | 10-1813222 | B1 | 12/2017 | | |
| KR | 10-1827322 | B1 | 2/2018 | | |
| KR | 10-1854855 | B1 | 5/2018 | | |
| WO | WO-2011/090821 | A2 | 7/2011 | | |
| WO | WO-2013192004 | A2 | * 12/2013 | ............. | A61K 8/064 |
| WO | WO-2018181126 | A1 | * 10/2018 | ........... | A45D 33/003 |

OTHER PUBLICATIONS

Aquarius Plastics "Mica", 2024, https://www.aquariusplastics.co.uk/glossary/mica/ (accessed Oct. 21, 2024) (Year: 2024).*
Database GNPD [Online] Jul. 13, 2017 (Jul. 13, 2017), anonymous: "Spot & Light Duo Pact SPF +PA+++", XP055860204, Database accession No. 4947515 * abstract *.
European Search Report from corresponding European Patent No. 19871148.3, Dated Nov. 19, 2021.
International Search Report from corresponding PCT Application No. PCT/KR2019/013211, dated Jan. 17, 2020.
Office Action from corresponding Japanese Patent Application No. 2021-545341, dated Apr. 14, 2022.
Office Action from corresponding Chinese Patent Application No. 201980066639.0, dated Nov. 18, 2023.
Office Action from corresponding Chinese Patent Application No. 201980066639.0, dated Apr. 12, 2024.

* cited by examiner

*Primary Examiner* — Bethany P Barham
*Assistant Examiner* — Judith Marie Kamm
(74) *Attorney, Agent, or Firm* — Harness, Dickey & Pierce, P.L.C.

(57) ABSTRACT

The present invention relates to a mesh-type moisture-release cushion cosmetic product and, more specifically, to a mesh-type moisture-release cushion cosmetic product having a cosmetic container, which has a mesh net mounted at the upper part thereof and is filled with a water-in-oil moisture-release cosmetic composition comprising: an oil phase part including wax, oil, and a mixture-emulsifying agent comprising a combination of a main emulsifying agent and an auxiliary emulsifying agent; a water phase part including water; and a powder part including hollow-structured gloss pigments.

6 Claims, 10 Drawing Sheets

MESH-TYPE MOISTURE-RELEASE CUSHION COSMETIC PRODUCT

CROSS-REFERENCE TO RELATED APPLICATIONS

This application is a national phase entry of PCT Application No. PCT/KR2019/013211, filed on Oct. 8, 2019, which claims the benefit and priority of Korean Patent Application No. 10-2018-0120175, filed on Oct. 10, 2018. The entire disclosure of the above applications is incorporated herein by references.

TECHNICAL FIELD

The present invention relates to a mesh-type moisture-release cushion cosmetic product and, more specifically, to a mesh-type moisture-release cushion cosmetic product comprising: a cosmetic container having a mesh net mounted at the upper part thereof; and a water-in-oil moisture-release cosmetic composition loaded into the container, wherein the water-in-oil moisture-release cosmetic composition comprises: an oil phase part including wax, oil, and a mixture-emulsifier comprising a combination of a main emulsifier and an auxiliary emulsifier, the main emulsifier including cetyl PEG/PPG-10/1 dimethicone and dimethicone/PEG-10/15 crosspolymer, the auxiliary emulsifier being at least one selected from the group consisting of lauryl PEG-9 polydimethylsiloxyethyl dimethicone, lauryl PEG-10 tris(trimethylsiloxy) silylethyl dimethicone, and sorbitan sesquioleate; an aqueous phase part including water; and a powder part including hollow-structured gloss pigments.

BACKGROUND ART

A makeup cosmetic composition is used to hide skin defects or to make the human body beautiful. When applied to the skin, the makeup cosmetic composition is required to be smoothly spread, have excellent adhesion to the skin and makeup effects, be free from shine after time, and maintain excellent stability to the skin.

In general, makeup cosmetic compositions are well known to be in an emulsion type, a powder type, or an oil-dispersed type. A powder-type composition causes high dryness in the skin while an oil-dispersed type contains a large amount of wax, which gives a heavy sensation of use and a suffocating feel.

Emulsion-type cosmetic compositions are largely divided into oil-in-water (O/W) and water-in-oil (W/O) types. Oil-in-water (O/W) type makeup cosmetics are poor in water resistance and easy to remove after being applied to the skin, and exhibit poor adhesion to the skin when containing powders.

Water-in-oil (W/O) type creams are superb in terms of makeup persistency and water resistance due to the outer oil phase thereof, but give a heavy and suffocating sensation of use due to the oil, and the emulsion is low in long-term stability. In addition, the powder breaks an oil and water balance in the skin to further dry the skin and increase sebum secretion, thus aggravating skin conditions.

The control of oil and water balance is very important for the skin. Particularly, when insufficient in moisture, the skin becomes dry and easily flaky, with trouble coming out.

As cosmetics for moisture supply, water-drop cosmetics have recently attracted the attention of consumers. The term "water-drop cosmetic" refers to a cosmetic that is designed to externally release the water contained therein when applied to the skin and thus form water drops on the skin, thereby replenishing the supply of sufficient moisture to the skin.

Korean Patent No. 10-2011-0048899 A relates to an invention titled "Water immediate release highly hydrous water-in-oil type foundation composition and manufacturing method therefor", disclosing that a water-in-oil type foundation emulsion contains a high content of the water phase therein and when the composition is applied to the skin, the emulsion is broken to immediately release the inner water phase, giving a fresh sensation to the skin. However, such a highly hydrous water-in-oil type water-release product causes phenomena of cracking, shrinkage, etc. as the moisture vaporizes and changes in the sensation of use. In order to solve the problems, development was made of a water-drop solid water-in-oil type cosmetic composition that employs wax, etc. as a solidifying agent to increase formulation stability and minimizes a component separation phenomenon therein (see Korean Patent No. 10-1813222).

In recent years, cushion pacts or cushion cosmetic products which have a cosmetic composition impregnated into a support made of a foam urethane or NBR spongy were developed (see Korean Patent No. 10-1159877). Allowing the user to conveniently carry and use flowable cosmetic formulations, such cushion cosmetic products have become popular in the cosmetic field.

However, when impregnated with a water-drop water-in-oil cosmetic composition using a solidifying agent such as wax, etc., sponge-type cushion cosmetic products have difficulty in releasing the cosmetic materials because the pores of the sponge are clogged by the cosmetic materials. Moreover, it is impossible to impregnate the sponge with the solid.

Thorough and intensive research, conducted by the present inventors with the aim of overcoming the problems encountered in the conventional techniques, culminated in the development of a low-hydrous water-in-oil moisture release cosmetic composition in which: a reduced content of water in the inner phase of the cosmetic composition guarantees the stability of the product and the cosmetic composition is associated with a mesh net-equipped cushion cosmetic container and evenly comes out through the mesh net, with drops of water bursting and being released, whereby an excellent makeup effect can be brought about.

SUMMARY

Technical Problem

Development, made in an effort to solve the problems of the prior art, has been directed to a water-in-oil type, solid-phase cosmetic composition that comprises a hollow-structured gloss pigment to control oil absorption for the oil phase contained therein, whereby the cosmetic composition exhibits an excellent moisture release effect despite a small amount of the inner phase unlike commercially available typical formulations, and secures hardness, a degree of water burst, and stability, leading to the present invention.

Therefore, the present invention is to provide a cosmetic composition which exhibits a makeup effect and stability satisfying the increased quality standard of consumers, and a mesh-type moisture-release cushion cosmetic product comprising a mesh-type cushion cosmetic container containing the composition.

Technical Solution

According to an aspect thereof, the present invention provides a mesh-type cushion cosmetic product comprising: a cosmetic container comprising a container body for receiving a cosmetic composition, and a mesh net mounted at an upper part of the container body; and a cosmetic composition loaded into the cosmetic container, wherein the cosmetic composition is a water-in-oil moisture release cosmetic composition comprising: an oil phase part including wax, oil, and a mixture-emulsifier comprising a combination of a main emulsifier and an auxiliary emulsifier, the main emulsifier including cetyl PEG/PPG-10/1 dimethicone and dimethicone/PEG-10/15 crosspolymer, the auxiliary emulsifier being at least one selected from the group consisting of lauryl PEG-9 polydimethylsiloxyethyl dimethicone, lauryl PEG-10 tris(trimethylsiloxy) silylethyl dimethicone, and sorbitan sesquioleate; an aqueous phase part including water; and a powder part including hollow-structured gloss pigments.

In the present invention, the "mesh-type cushion cosmetic product", which is used as opposed to conventional "sponge-type cushion cosmetic product", has a structure in which a cosmetic composition is not impregnated into a spongy, but just positioned under the mesh net, and the mesh net resiliently moves in the vertical direction to give a cushion sensation, and the cosmetic composition is released through the mesh net when the mesh net is pressed by a hand or a puff (see Korean Utility Nos. 20-2015-0000973 A and 20-2016-0002585 A and Korean Patent No. 10-1541396).

In the mesh-type moisture-release cushion cosmetic product provided according to an embodiment of the present invention, the cosmetic composition is a low-hydrous, water-in-oil moisture release cosmetic composition in which the aqueous phase part is contained at a content of 25-45% by weight. In contrast to conventional high-hydrous water-drop cosmetic formulations, the water-in-oil type cosmetic composition of the present invention is characterized by an excellent moisture release effect despite a small amount of the inner phase.

In an embodiment of the present invention, the cosmetic composition may contain 35-60% by weight of the oil phase part, 25-45% by weight of the aqueous phase part, and 5-25% by weight of the powder part, based on the total weight thereof. In the cosmetic composition, for example, the oil phase part may contain 3-8% by weight of a mixed emulsifier, 15-25% by weight of an organic ultraviolet filter, 5-15% by weight of wax, and 10-20% by weight of an oil; the powder part may contain 2-8% by weight of color and extender pigments, 3-15% by weight of an inorganic ultraviolet filter, and 0.5-4% by weight of a hollow-structured gloss pigment, and the aqueous phase part may account for the balance.

In the mesh-type moisture-release cushion cosmetic product provided according to an embodiment of the present invention, the hollow-structured gloss pigment of the powder part is manufactured by coating a planar flake substrate with a metal oxide and then removing the central planar flakes through acid treatment and alkali treatment on the coated substrate. With respect to a method for manufacturing a hollow structured gloss pigment, reference may be made to Korean Patent No. 10-2017-0055580 A, the disclosure of which is incorporated herein.

In an embodiment of the present invention, the hollow-structured gloss pigment is a hollow white pearlescent pigment (composition: titanium dioxide (96%), tin oxide (1%), and silica (3%)). This pigment is dispersed in the outer phase of the W/S type composition. When a water drop type solid balm is broken, the water of the inner phase bursts and is instantly absorbed by the white pearl pigment dispersed in the outer phase, with the consequent expression of white (pearl) drops.

The advantages of the hollow-structured gloss pigment of the present invention are as follows: the gloss pigment can reduce an oily sensation in a complete formulation, compared to other powder because the white pearlescent pigment has a hollow form; silica applied to the surface of the pigment raises oil absorption ability, thus increasing the adhesion of the pigment to the skin upon makeup; and the gloss pigment has a light sensation of use, compared to conventional titanium dioxide substrates and shows a sun-boosting effect because most of the white pearlescent pigment is accounted for by titanium dioxide.

In the following Example, when the hollow pearlescent pigment of the present invention, (non-hollow) shimmer pearls, and non-coated $TiO_2$ were added to the same formulation and observed for the formation of white drops, the (non-hollow) shimmer pearls and the non-coated $TiO_2$ remarkably decreased in white saturation and water burst phenomenon, compared to the hollow pearls used in the present invention (see FIG. 5). Presumably, this is because the hollow pearls present in the outer phase absorb the water of the inner phase, compared to the non-hollow pearls, to increase the water drop phenomenon.

In the mesh-type moisture-release cushion cosmetic product provided according to an embodiment of the present invention, the wax includes at least one selected from the group consisting of candelilla wax, carnauba wax, beeswax, C30-45 alkyl methicone, C30-45 alkyl dimethicone, C30-45 alkyldimethylsilyl polypropylsilsesquioxane, ceresin, polyethylene, ozokerite, and myristyl myristate.

In the present invention, the wax plays a role as a solidifying agent and forms a wax-gel network to safely store the water of the inner phase. In addition, the wax is dispersed in the outer phase and contributes to the formation of white drops when the hollow-structured gloss pigments are discharged outside the mesh net, with the water entrapped therein, by pressure application (see FIG. 4)

In the mesh-type moisture-release cushion cosmetic product provided according to an embodiment of the present invention, the oil includes at least one selected from the group consisting of cyclomethicone, dimethicone, dimethicone/vinyl dimethicone crosspolymer, phenyl trimethicone, polyisobutene, squalane, cetyl ethylhexanoate, caprylic/capric triglyceride, coco caprylate/caprate, octyldodecanol, dicaprylyl carbonate, triethylhexanoin, olive oil, and macadamia seed oil.

In the mesh-type moisture-release cushion cosmetic product provided according to an embodiment of the present invention, the aqueous phase part may further comprise at least one of a moisturizer, a thickener, and an additive. The moisturizer may include, for example, glycerin, polyglycerin, propylene glycol, butylene glycol, and the like. The thickener may include, for example, carbomer, xanthan gum, and the like.

In the mesh-type moisture-release cushion cosmetic product provided according to an embodiment of the present invention, the powder part may further comprise at least one of an extender pigment, a color pigment, and an inorganic ultraviolet filter. The extender pigment may include, for example, talc, mica, sericite, silica, calcium carbonate, kaolin, etc. The color pigment may include, for example, yellow iron oxide, red iron oxide, black iron oxide, etc. The inorganic ultraviolet filter may include titanium dioxide, zinc oxide, etc.

In the mesh-type moisture-release cushion cosmetic product provided according to an embodiment of the present invention, the mesh net may have a pore size of 0.1-2 mm, preferably 0.5-1.5 mm, and most preferably 1.0 mm. Given the range of pore sizes, the mesh allows the content of the cosmetic composition to be discharged in proper mixture with water therethrough. Too small a pore size does not discharge the content, but only water bursts out of the mesh net. When the pore size is too large, the cosmetic composition may flow out too much, contaminating the cosmetic container (see FIG. 6)

In the mesh-type moisture-release cushion cosmetic product provided according to an embodiment of the present invention, when the solid balm of the cosmetic composition present under the mesh net is broken in response to the compression of the mesh net by a finger or a puff, the water of the inner phase bursts outand is instantly absorbed by the hollow-structured gloss pigment dispersed in the outer phase, with the consequent formation and exudation of white (pearl) drops out of the mesh net.

Advantageous Effects

According to the present invention, the cosmetic composition has an excellent moisture release effect in spite of a low content of the inner phase, maintains properties even after storage for a long period of time or under a temperature change, and is thus provided with reinforced storage stability and formulation stability, whereby the cosmetic composition overcomes the problem that conventional highly hydrous water-in-oil moisture release product becomes poor in the sensation of use with the evaporation of moisture therefrom. In addition, the cosmetic composition is combined with a mesh-type cushion cosmetic container, so that when the solid balm of the cosmetic composition present under the mesh net is broken in response to the compression of the mesh net by a finger or a puff, the water of the inner phase bursts out and is instantly absorbed by the hollow-structured gloss pigment dispersed in the outer phase, with the consequent formation and exudation of white (pearl) drops out of the mesh net. This can give an excellent water drop effect substantially and visually to the user.

DETAILED DESCRIPTION

Figure 1A:
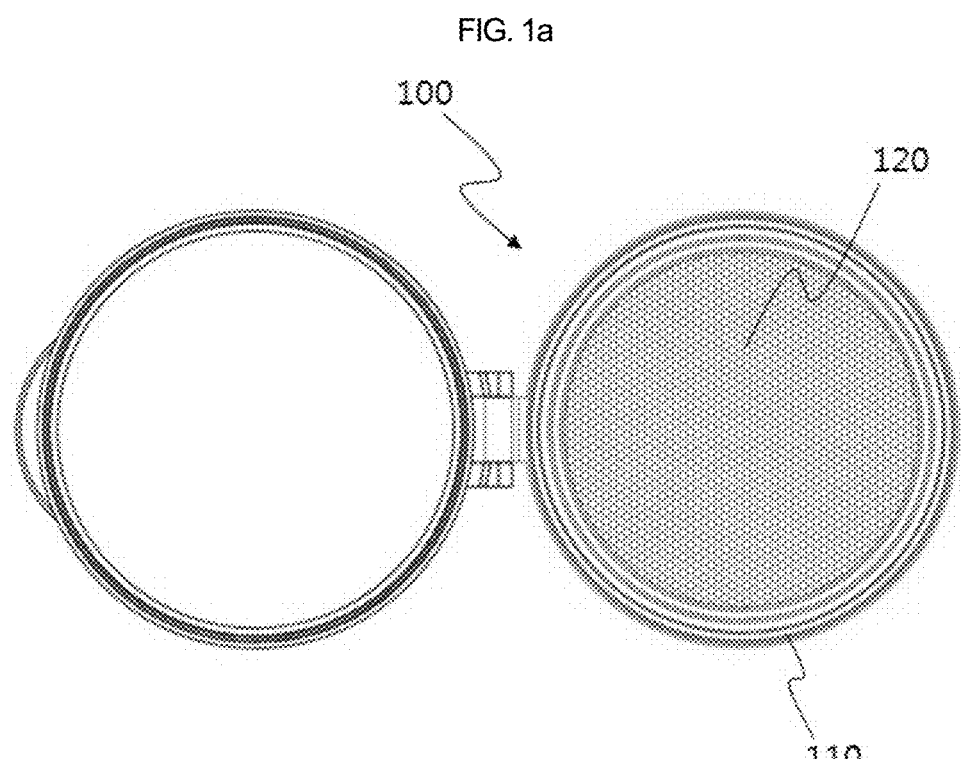
FIGS. 1a and 1b depict a mesh net-mounted cosmetic container for use in a mesh-type moisture-release cushion cosmetic product according to an embodiment of the present invention.

Below, a detailed description will be given of the present invention with reference to Examples. These Examples are set forth to illustrate the present invention, but should not be construed to limit the scope of the present invention.

Examples 1 to 5 and Comparative Examples 1 to 4: Preparation of Cosmetic Composition Of the ingredients listed in Table 1, below, oil phases A (wax)+B (emulsifier)+C (oil), and UV filter B (organic UV filter) were heated and completely dissolved at 80° C. To the completely dissolved oil phase, pulverization-treated powder A (color pigment and extender pigment)+UV filter A (inorganic UV filter) were added, and then dispersed by stirring. Aqueous phase A (moisturizer, additive)+B (purified water) were heated and completely dissolved at 80° C. The aqueous phase thus obtained was slowly added to the oil phase part in mixture with the powder to perform emulsification. After emulsification, powder B (hollow-structured gloss pigment, etc.) was added and uniformly dispersed. As for powder B, hollow-structured gloss pigments (PT-9001K from CQV) was used in the Examples while the Comparative Examples employed shimmer pearls A and B, which are pearlescent pigments with average particle diameters of 12 µm and 24 µm, respectively, and non-coated $TiO_2$ A and B, which are $TiO_2$ particles for pigments with average particle diameters of 0.2 µm and 0.3 µm, respectively.

TABLE 1

| Class | Ingredient | Example No. (wt %) | | | | | Comparative Example No. (wt %) | | | |
|---|---|---|---|---|---|---|---|---|---|---|
| | | 1 | 2 | 3 | 4 | 5 | 1 | 2 | 3 | 4 |
| Oil phase A | C30-45 alkyldimethylsilyl-polypropylsilsesquioxane | 1.50 | 1.50 | 1.50 | 1.50 | 1.50 | 1.50 | 1.50 | 1.50 | 1.50 |
| | Ceresin | 2.50 | 2.50 | 2.50 | 2.50 | 2.50 | 2.50 | 2.50 | 2.50 | 2.50 |
| | Polyethylene | 0.50 | 0.50 | 0.50 | 0.50 | 0.50 | 0.50 | 0.50 | 0.50 | 0.50 |
| | Candelilla wax | 2.00 | 2.00 | 2.00 | 2.00 | 2.00 | 2.00 | 2.00 | 2.00 | 2.00 |
| | Myristyl myristate. | 1.50 | 1.50 | 1.50 | 1.50 | 1.50 | 1.50 | 1.50 | 1.50 | 1.50 |
| Oil phase B | Cetyl PEG/PPG-10/1 dimethicone | 0.80 | 0.80 | 0.80 | 0.80 | 0.80 | 0.80 | 0.80 | 0.80 | 0.80 |
| | Dimethicone/PEG-10/15 crosspolymer | 1.50 | 1.50 | 1.50 | 1.50 | 1.50 | 1.50 | 1.50 | 1.50 | 1.50 |
| | Lauryl PEG-9 polydimethylsiloxyethyl | | — | 0.80 | | 1.50 | 0.80 | 0.80 | 0.80 | 0.80 |

TABLE 1-continued

| Class | Ingredient | Example No. (wt %) | | | | | Comparative Example No. (wt %) | | | |
|---|---|---|---|---|---|---|---|---|---|---|
| | | 1 | 2 | 3 | 4 | 5 | 1 | 2 | 3 | 4 |
| | dimethicone | | | | | | | | | |
| | Lauryl PEG-10 tris(trimethylsiloxy)silylethyl dimethicone | | 1.50 | | 0.80 | | | | | |
| | Sorbitan sesquioleate | 1.50 | | 0.80 | 0.80 | | 0.80 | 0.80 | 0.80 | 0.80 |
| Oil phase C | Phenyl trimethicone | 3.00 | 3.00 | 3.00 | 3.00 | 3.00 | 3.00 | 3.00 | 3.00 | 3.00 |
| | Dimethicone | 2.00 | 2.00 | 2.00 | 2.00 | 2.00 | 2.00 | 2.00 | 2.00 | 2.00 |
| | Dimethicone/vinyl dimethicone crosspolymer | 1.00 | 1.00 | 1.00 | 1.00 | 1.00 | 1.00 | 1.00 | 1.00 | 1.00 |
| | Cyclomethicone | 6.00 | 6.00 | 6.00 | 6.00 | 6.00 | 6.00 | 6.00 | 6.00 | 6.00 |
| | Coco caprylate/caprate | 2.00 | 2.00 | 2.00 | 2.00 | 2.00 | 2.00 | 2.00 | 2.00 | 2.00 |
| Powder A | Yellow iron oxide, red iron oxide, black iron oxide, extender pigment | 5.00 | 5.00 | 5.00 | 5.00 | 5.00 | 5.00 | 5.00 | 5.00 | 5.00 |
| Inorganic UV filter | Titanium dioxide | 8.00 | 8.00 | 8.00 | 8.00 | 8.00 | 8.00 | 8.00 | 8.00 | 8.00 |
| Organic UV filter | Ethylhexyl methoxycinnamate | 6.50 | 6.50 | 6.50 | 6.50 | 6.50 | 6.50 | 6.50 | 6.50 | 0.50 |
| | Ethylhexyl salicylate | 4.50 | 4.50 | 4.50 | 4.50 | 4.50 | 4.50 | 4.50 | 4.50 | 4.50 |
| | Octocrylene | 3.00 | 3.00 | 3.00 | 3.00 | 3.00 | 3.00 | 3.00 | 3.00 | 3.00 |
| | Homosalate | 5.00 | 5.00 | 5.00 | 5.00 | 5.00 | 5.00 | 5.00 | 5.00 | 5.00 |
| Aqueous phase A | Moisturizer and additive | 10.00 | 10.00 | 10.00 | 10.00 | 10.00 | 10.00 | 10.00 | 10.00 | 10.00 |
| Aqueous phase B | Purified water | To 100 | To 100 | To 100 | To 100 | To 100 | To 100 | To 100 | To 100 | To 100 |
| Powder B | Hollow-structure gloss pigment | 0.50 | 0.80 | 1.00 | 2.00 | 3.00 | | | | |
| | Shimmer pearl A | | — | | | | 1.00 | | | |
| | Shimmer pearl B | | — | | | | | 1.00 | | |
| | Non-coating $TiO_2$ A | | — | | | | | | 1.00 | |
| | Non-coating $TiO_2$ B | | — | | | | | | | 1.00 |

Preparation Example 1: Manufacture of Mesh Net-Type Cushion Cosmetic Product

Figure 1B:
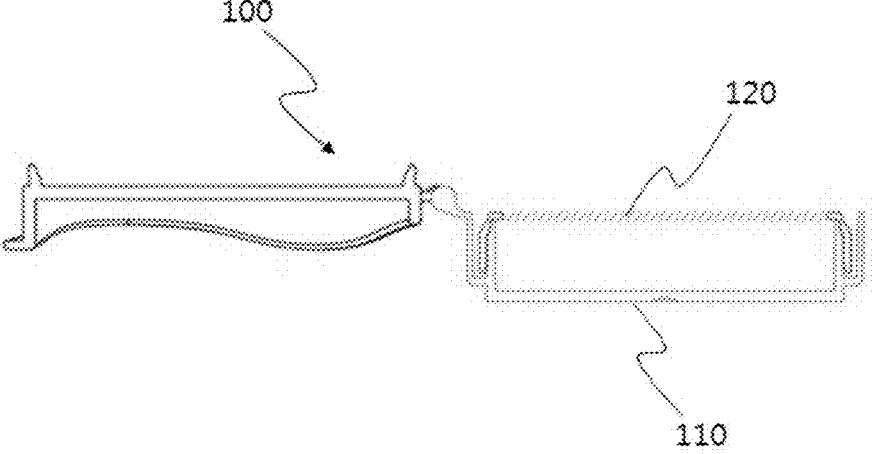
Figure 2:
FIG. 2 is a photographic image of a mesh-type moisture-release cushion cosmetic product according to the present invention. When the mesh net is pressed, white (pearl) water drops are obviously visualized.
Figure 3:
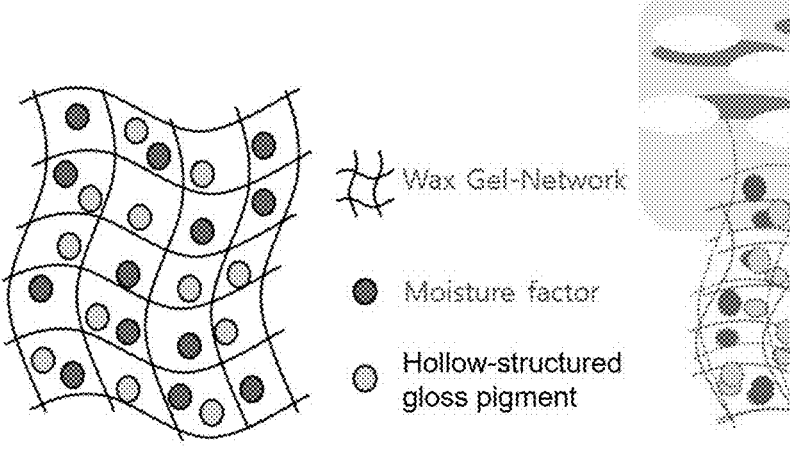
FIG. 3 is a schematic diagram illustrating the mechanism of forming white (pearl) water drops in the water-in-oil moisture release cosmetic composition according to the present invention.

The cosmetic compositions prepared according to the Examples and the Comparative Examples were in the form of solid balm formulations and thus were loaded in a high temperature state of 70-80° C. into mesh net-mounted cosmetic containers to manufacture mesh net-type cushion cosmetic products. FIG. 1 depicts a mesh net-mounted cosmetic container for use in a mesh-type moisture-release cushion cosmetic product according an embodiment of the present invention (100: cosmetic container, 110: container body, and 120: mesh net). The container body (110) of the cosmetic container (100) depicted in FIG. 1 was filled with the cosmetic composition on which the mesh net (120) was then mounted to manufacture a mesh net-type cushion cosmetic product. FIG. 2 is a photographic image of a mesh-type moisture-release cushion cosmetic product according to the present invention. When the mesh net was pressed, white (pearl) water drops appeared clearly.

Figure 4:
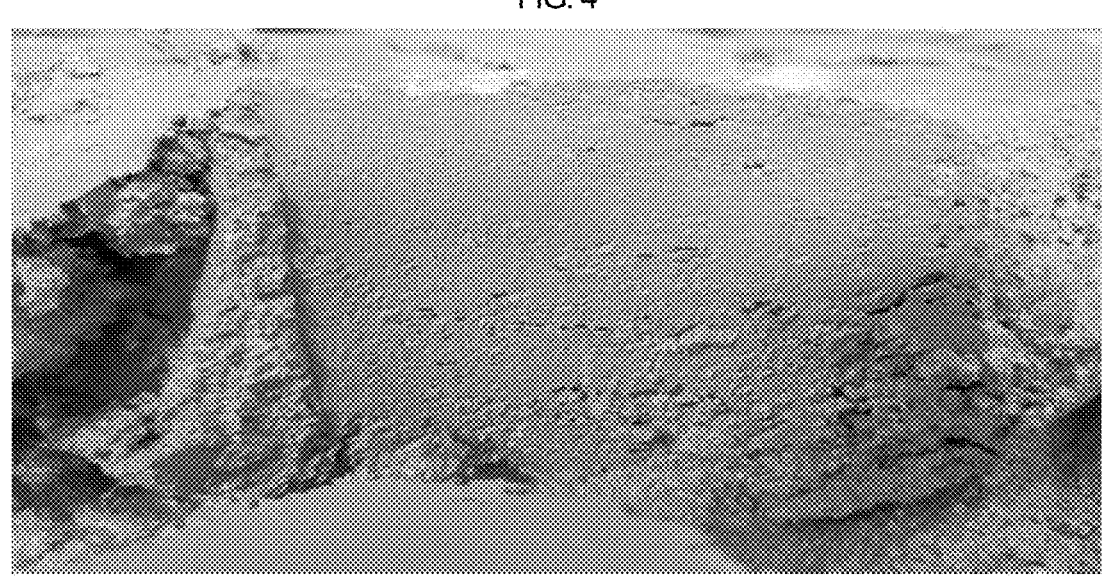
FIG. 4 is a photographic image of a cross section of the loaded water-in-oil moisture release cosmetic composition according to the present invention.

Experimental Example 1: Comparison. Of Water-Drop Effect According to Type of Pearlescent Pigment The cosmetic compositions prepared according to the Examples could be observed with the naked eye to exhibit a water drop effect. FIG. 4 is a photographic image of a cross section of the loaded water-in-oil moisture release cosmetic composition according to the present invention.

In order to compare water-drop effects according to types of pearlescent pigments, the composition of Example 3 which was high in dispersion stability as a result of the effective action of the emulsifier was used as a reference. Corresponding to the hollow-structured gloss pigment, 1% of each of Shimmer pearl A, Shimmer pearl B, non-coating $TiO_2$ A, and non-coating $TiO_2$ B were applied to the same process. Then, the compositions thus obtained were loaded to aluminum chalets in the condition of 80° C. and solidified at room temperature. Thereafter, observation was made of the formation of white drops while the surfaces were scraped.

Figure 5:
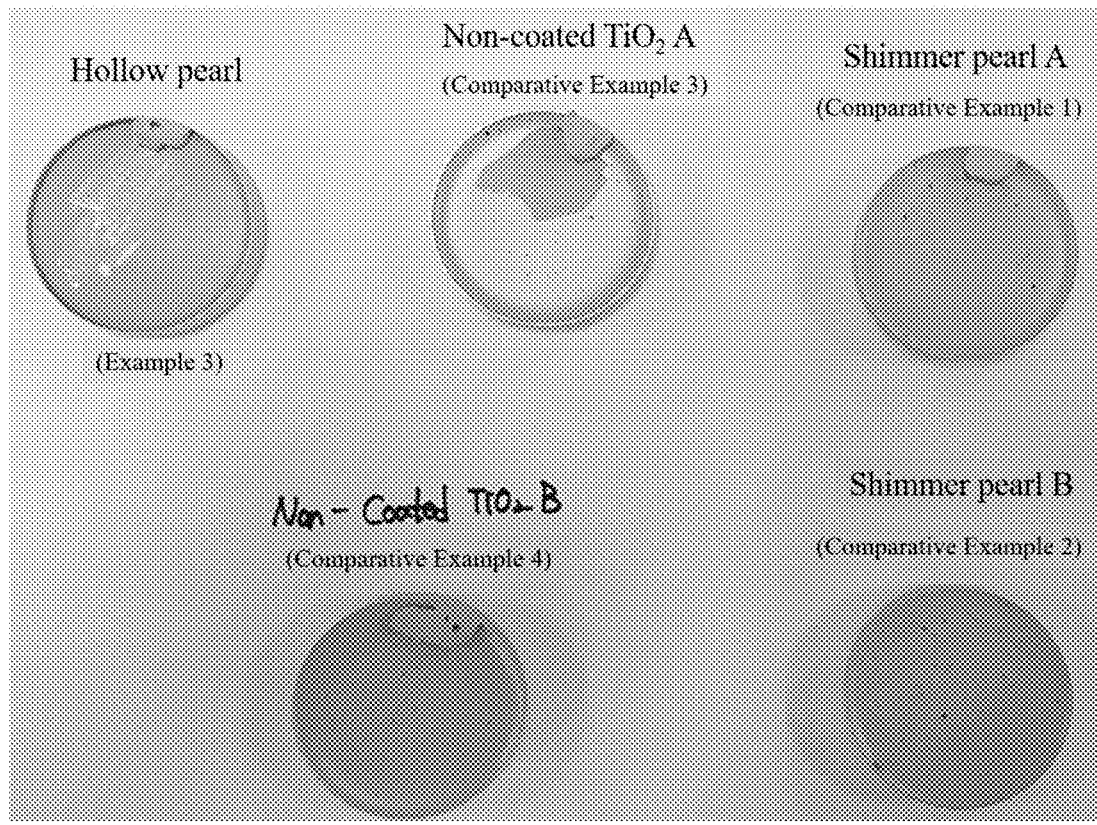
FIG. 5 is a photographic image showing comparison of degrees of white drop formation after the hollow pearl, the (non-hollow) Shimmer pearls, and the non-coated $TiO_2$ were added in the same amount.
Figure 6A:
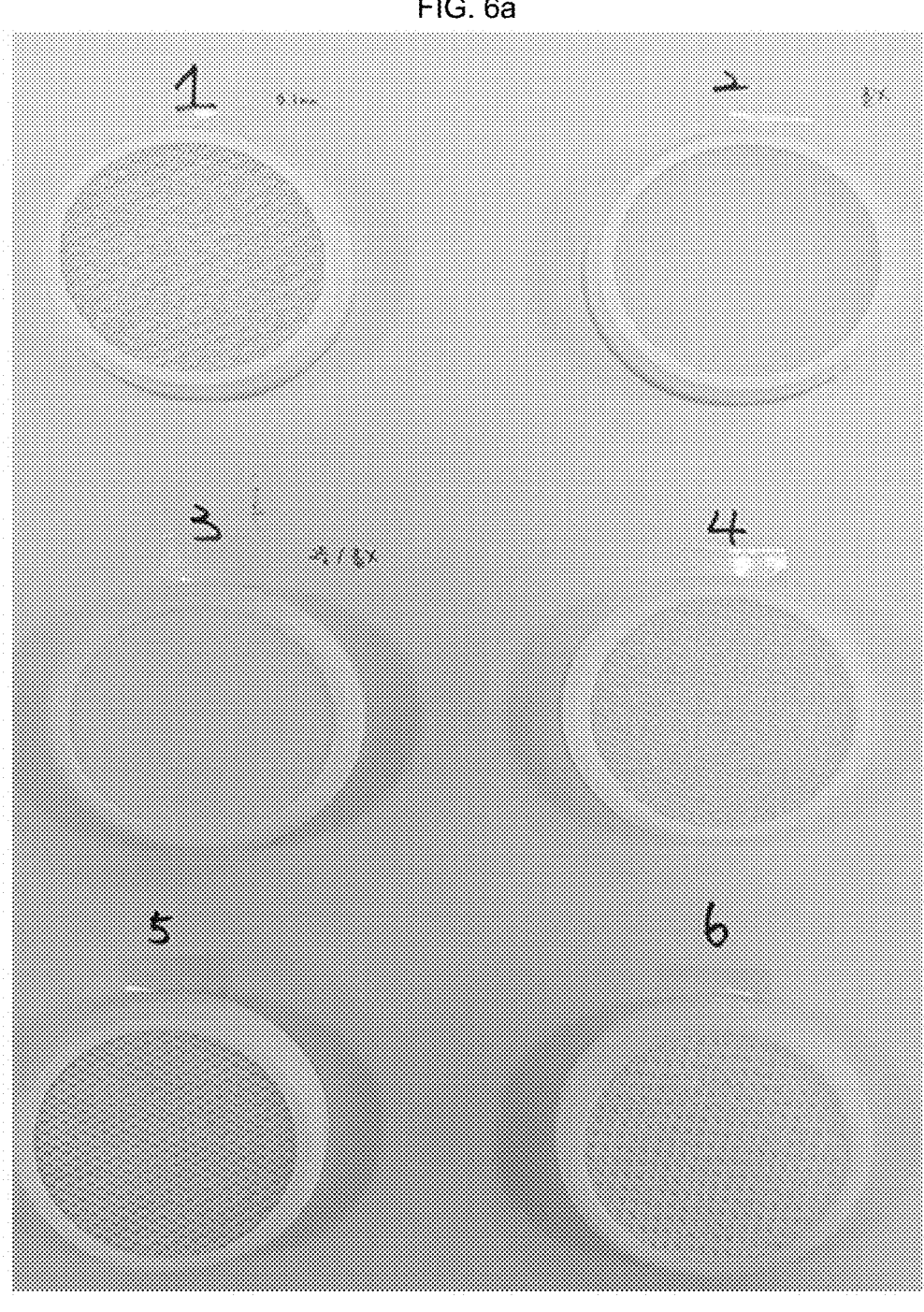
FIGS. 6a, 6b, 6c, 6d, 6e, 6f, 6g and 6h are photographic images of the mesh-type moisture-release cushion cosmetic products of the present invention for comparison of water drop effects according to mesh size.
Figure 6B:
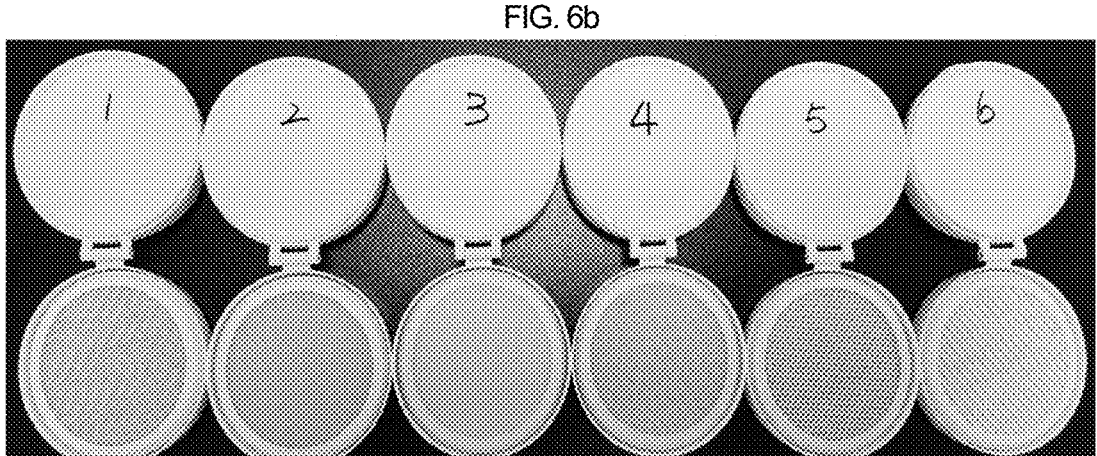
Figure 6C:
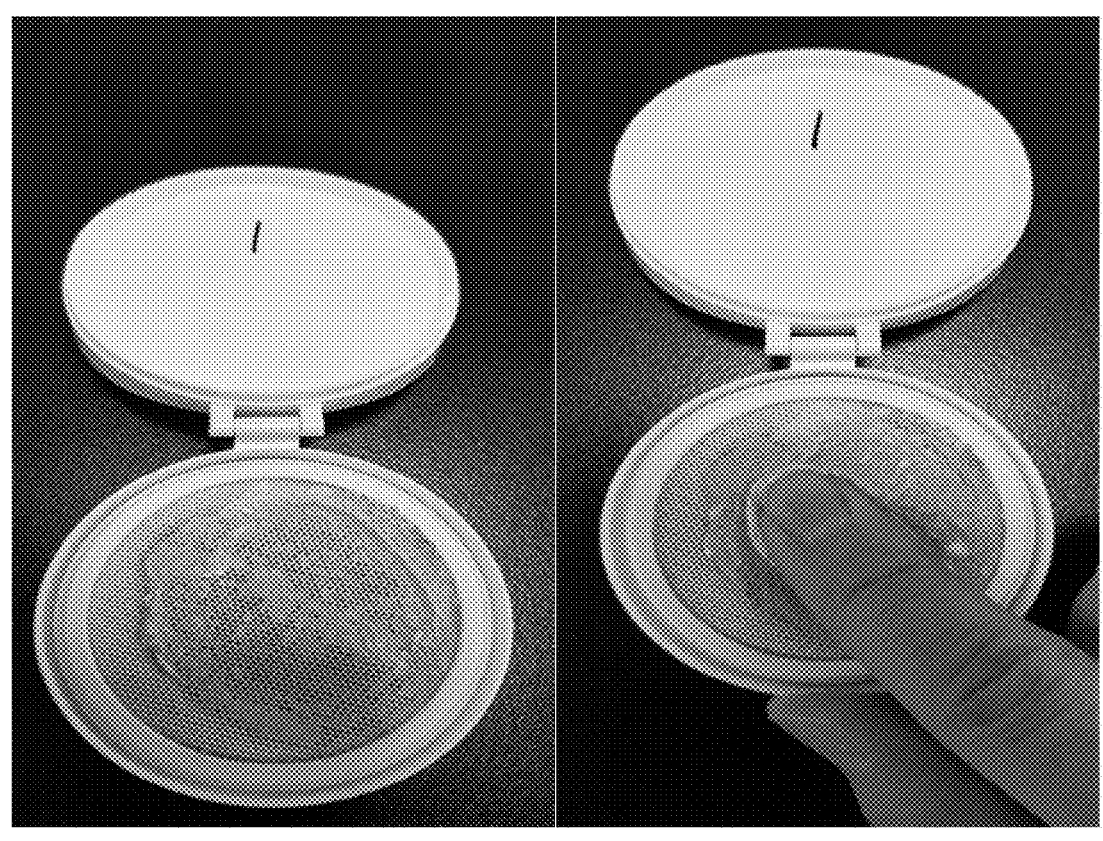
Figure 6D:
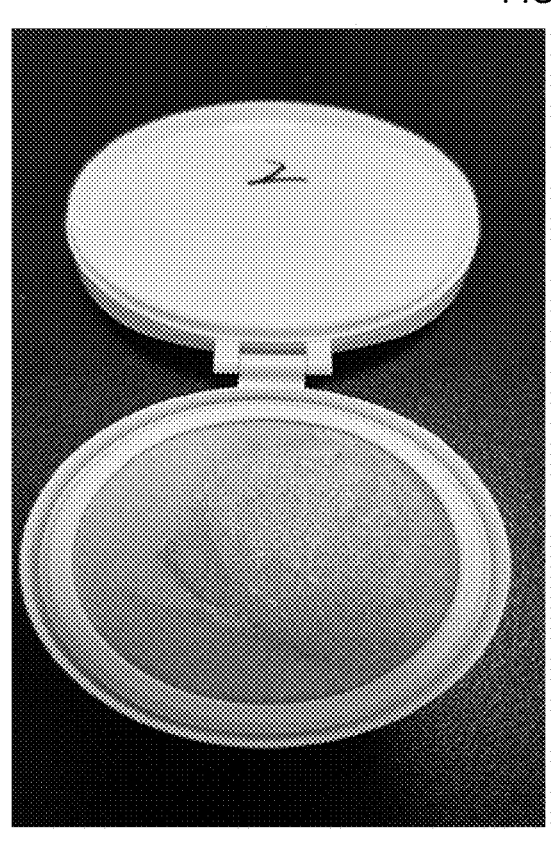
Figure 6D:
Figure 6E:
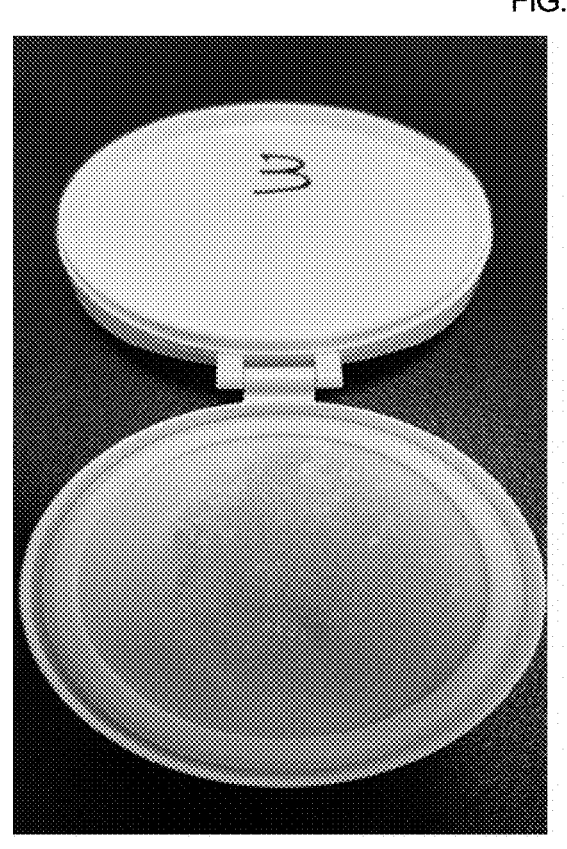
Figure 6E:
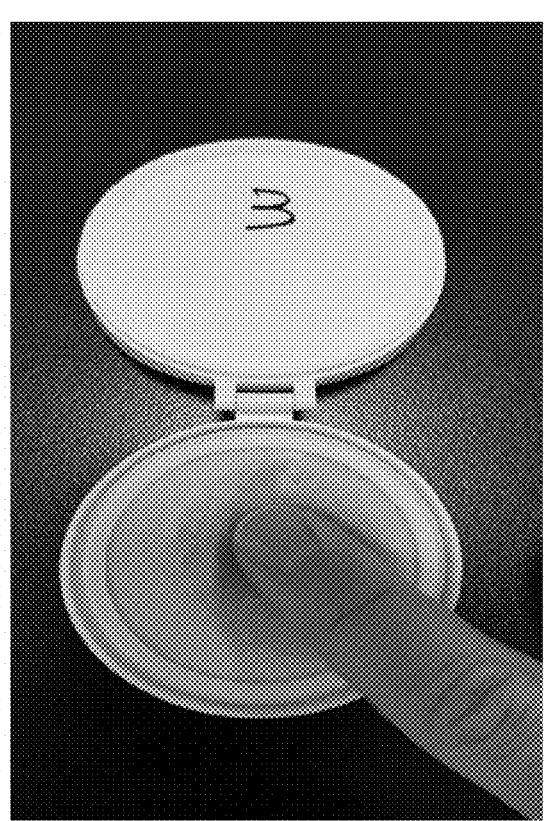
Figure 6F:
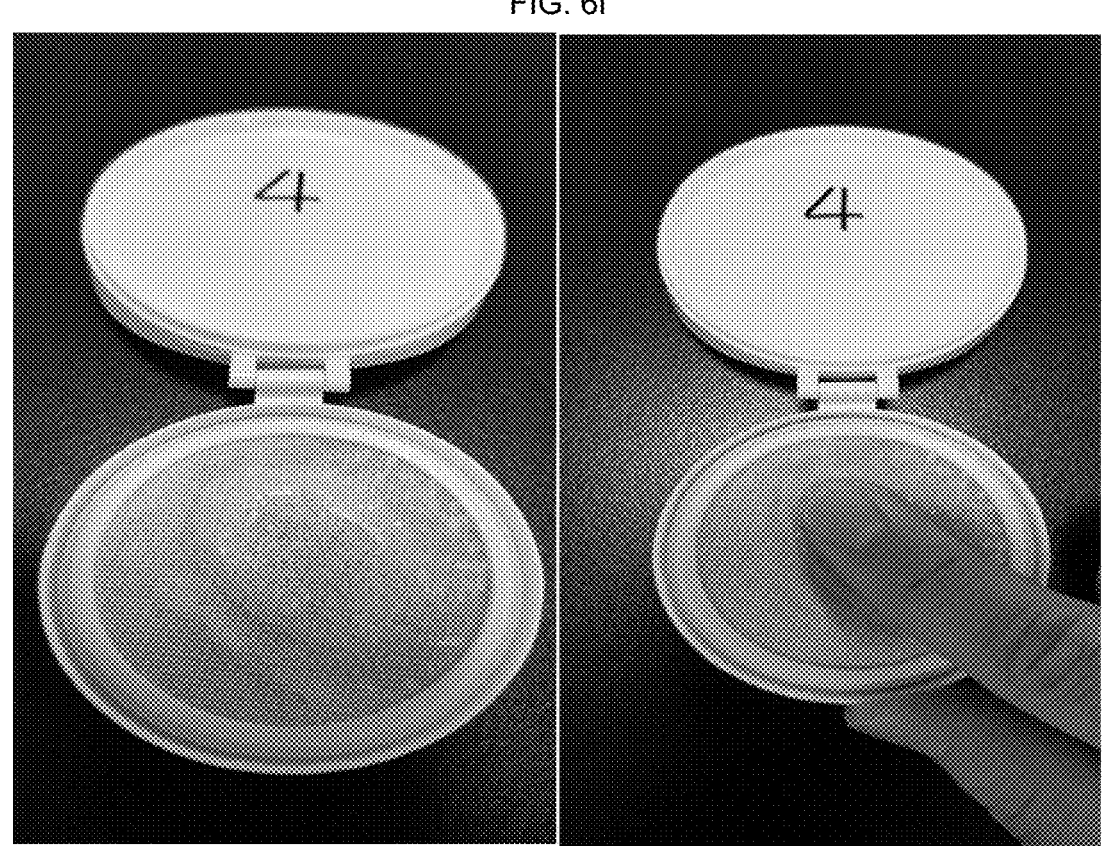
Figure 6G:
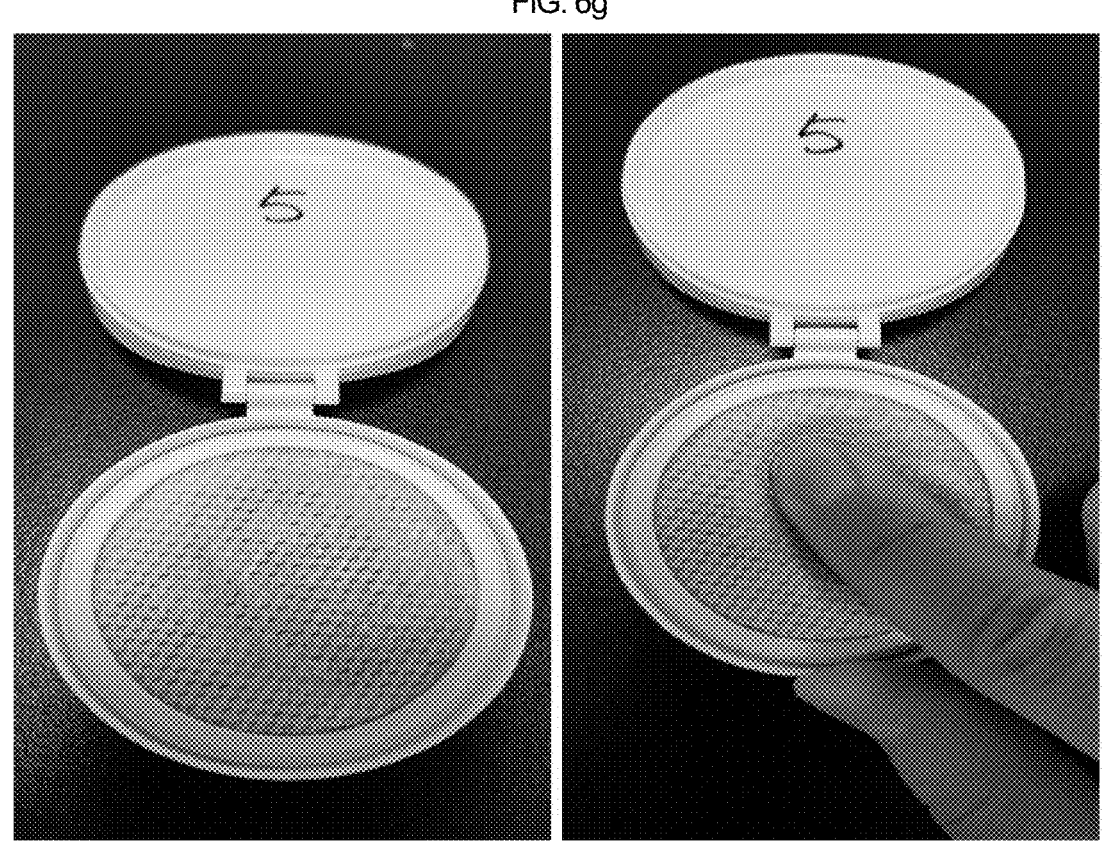
Figure 6H:
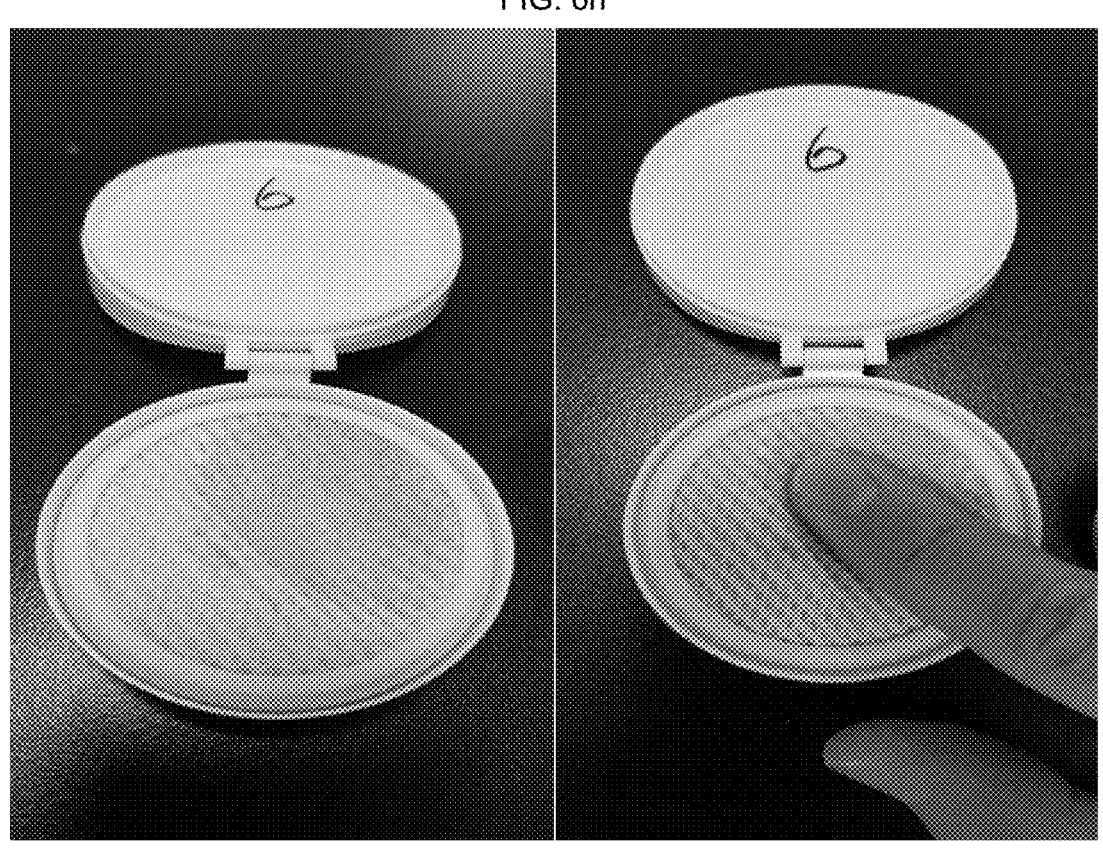

FIG. 5 is a photographic image showing comparison of degrees of white drop formation after the hollow pearl, the (non-hollow) Shimmer pearls, and the non-coating $TiO_2$ were added in the same amount. As a result, the degree of formation of white drops was in the order of hollow-structured gloss pigment >Shimmer pearl >Non-coating $TiO_2$. Water drops appeared most obviously from the hollow-structured gloss pigment. Although appeared, water drops were formed very slightly for the Shimmer pearls. No water drops were found from the non-coating $TiO_2$.

Experimental Example 2: Comparison of Water-Drop Effect According to Mesh Size and Shape In order to exhibit the moisture release characteristic of the formulation as much as possible, the effect was maximized by covering the formulation with a mesh net. The formation of white drops was observed according to mesh size and shape. As the mesh net shapes, a stocking-like mesh net the pore size of which could not be determined with the naked eye, a single mesh, a double mesh, and an embossed mesh were contemplated. Sizes with 0.1 mm-2 mm were applied to the mesh.

According to a criterion for the uniform release of the composition and white drops, a use test was carried out and evaluated with the naked eye.

FIG. 6 shows photographic images of the mesh-type moisture-release cushion cosmetic products of the present invention for comparison of water drop effects according to mesh size. In FIG. 6, No. 1 accounts for a single mesh type with a pore size of 1 mm, No. 2 for a single mesh type with a pore size of 0.1 mm, No. 3 for a double mesh type with a pore size of 0.1 mm, No. 4 for a single mesh type with a pore size of 0.5 mm, No. 5 for a thick mesh pattern with a pore size of 2 mm, and No. 6 for an embossed mesh type with a pore size of 2 mm.

The best test result was obtained in the single mesh type, which is resilient. A thicker mesh, e.g., a double mesh, resulted in a smaller release amount of the cosmetic content and thus was not suitable for makeup cosmetic products. In addition, a denser mesh net made it more difficult to discharge the cosmetic content and allowed the elution of only white drops therefrom, thus resulting in an insufficient cosmetic effect. More of the content was applied to the face through a looser mesh net which is thus unsuitable for use in makeup cosmetic products. In FIG. 6, the mesh of No. 1 allowed the content and water to be most uniformly released in the white drop pattern. Through the mesh of No. 4, the content and water were smoothly released although to a lesser degree than the mesh of No. 1. Based on the test data, a resilient single mesh type with a pore size of 0.5-1.5 mm was determined to be the most suitable for releasing the content and forming white drops.

Although some embodiments have been disclosed above, it should be understood that these embodiments are given by way of illustration only, and that various modifications, variations, and alterations can be made without departing from the spirit and scope of the present invention. Therefore, the scope of the present invention should be limited only by the accompanying claims and equivalents thereof.

DESCRIPTION OF NUMERALS IN THE DRAWING

100: Cosmetic container
110: Container body
120: Mesh net

What is claimed is:

1. A mesh-type moisture-release cushion cosmetic product, comprising: a cosmetic container comprising a container body for receiving a cosmetic composition, and a mesh net mounted at an upper part of the container body; and a cosmetic composition loaded into the cosmetic container in a form of a solid balm, wherein the cosmetic composition is a water-in-oil moisture release cosmetic composition comprising: an oil phase part including wax, oil, and a mixture-emulsifier comprising a combination of a main emulsifier and an auxiliary emulsifier, the main emulsifier including cetyl PEG/PPG-10/1 dimethicone and dimethicone/PEG-10/15 crosspolymer, the auxiliary emulsifier including lauryl PEG-9 polydimethylsiloxyethyl dimethicone, and sorbitan sesquioleate; an aqueous phase part including water; and a powder part including a hollow-structured gloss pigment, wherein the cosmetic composition is a water-in-oil moisture release cosmetic composition containing the aqueous phase part at a content of 25-45% by weight, and the hollow-structured gloss pigment at a content of 1-4% by weight, wherein the mesh net has a pore size of 1.0-1.5 mm, wherein the hollow-structured gloss pigment comprises a hollow white pearlescent pigment comprising titanium dioxide, tin oxide, and silica, wherein the hollow-structured gloss pigment is dispersed in the oil phase part of the composition, and wherein when the solid balm of the cosmetic composition present under the mesh net is broken in response to the compression of the mesh net by a finger or a puff, the water of the aqueous phase part bursts out and is instantly absorbed by the hollow-structured gloss pigment dispersed in the oil phase part, with the consequent formation and exudation of white drops out of the mesh net.

2. The mesh-type moisture-release cushion cosmetic product of claim 1, wherein the hollow-structured gloss pigment of the powder part is manufactured by coating a planar flake substrate with a metal oxide and then removing central planar flakes through acid treatment and alkali treatment on the coated substrate.

3. The mesh-type moisture-release cushion cosmetic product of claim 1, wherein the wax includes at least one selected from the group consisting of candelilla wax, carnauba wax, beeswax, C30-45 alkyl methicone, C30-45 alkyl dimethicone, C30-45 alkyldimethylsilyl polypropylsilsesquioxane, ceresin, polyethylene, ozokerite, and myristyl myristate.

4. The mesh-type moisture-release cushion cosmetic product of claim 1, wherein the oil includes at least one selected from the group consisting of cyclomethicone, dimethicone, dimethicone/vinyl dimethicone crosspolymer, phenyl trimethicone, polyisobutene, squalane, cetyl ethylhexanoate, caprylic/capric triglyceride, coco caprylate/caprate, octyldodecanol, dicaprylyl carbonate, triethylhexanoin, olive oil, and macadamia seed oil.

5. The mesh-type moisture-release cushion cosmetic product of claim 1, wherein the aqueous phase part further comprises at least one of a moisturizer, a thickener, and an additive.

6. The mesh-type moisture-release cushion cosmetic product of claim 1, wherein the powder part further comprises at least one of an extender pigment, a color pigment, and an ultraviolet filter.

* * * * *